United States Patent [19]

Cramp et al.

[11] Patent Number: 4,600,310

[45] Date of Patent: Jul. 15, 1986

[54] OPTICAL FIBRE SENSOR

[75] Inventors: John H. W. Cramp, St Helens; Robert F. Reid, Runcorn, both of England

[73] Assignee: Imperial Chemical Industries PLC, London, England

[21] Appl. No.: 363,228

[22] Filed: Mar. 29, 1982

[30] Foreign Application Priority Data

Mar. 30, 1981 [GB] United Kingdom ................. 8109913

[51] Int. Cl.⁴ ............................................. G01N 21/59
[52] U.S. Cl. ................................. 356/432; 350/96.29; 350/436
[58] Field of Search ............... 350/96.29, 96.30, 96.33, 350/96.34; 356/128, 432; 250/357.1

[56] References Cited

U.S. PATENT DOCUMENTS 3,068,742 12/1962 Hicks et al. .
4,200,110 4/1980 Peterson et al. .................. 356/39 X

FOREIGN PATENT DOCUMENTS 1959612 6/1971 Fed. Rep. of Germany .
2255300 5/1974 Fed. Rep. of Germany .

OTHER PUBLICATIONS

Laser Focus/Electro-Optics, "Award-Winning Fiber Temperature Sensor Slated for Commercial Production", Dec. 1983.
Analytical Letters, vol. 9, No. 4, 1976, New York D. J. David et al. "Direct Measurement of Ammonia in Ambient Air" pp. 389 to 404.
Nature, vol. 257, Oct. 23, 1975 London E. E. Hardy et al. "Coated Optical Guides for Spectrophotometry of Chemical Reactions" pp. 666 to 667.
Analytical Chemistry, vol. 51, No. 4, Apr. 1979, Columbus, OH, USA P. L. Smock et al. "Vapor Phase Determination of Blood Ammonia by an Optical Waveguide Technique" pp. 505 to 508.

*Primary Examiner*—Bruce Y. Arnold
*Attorney, Agent, or Firm*—Cushman, Darby & Cushman

[57] ABSTRACT

An apparatus for detecting changes in chemical or physical parameters, comprises a sensing optical fibre having a core surrounded by a relatively sensitive cladding the absorption spectrum of which varies with changes in chemical or physical parameters when these are applied to the cladding, and a transmissive optical fibre having a core surrounded by a relatively insensitive cladding for connecting at least one end of the sensing optical fiber to a remote light source and a remote detector. The core of the sensing optical fibre has substantially the same diameter as the core of the transmissive fibre and the refractive indices of both the relatively sensitive and the relatively insensitive claddings are less than the refractive indices of the cores of both the sensing optical fibre and the transmissive optical fibre. The transmissive optical fibre can be made up of two optical fibres, one extending from each end of the sensing optical fibre to be connected at their remote ends to a light source and detector respectively. Alternatively, a single optical fibre may extend from one end of the sensing optical fibre, the other end of which is made reflective, the single transmissive fibre being connected to both sources and detector using a beam splitter. The apparatus may be provided in the configuration of a probe having a reflective sensitive end, with one or more transmissive fibres extending for connection to a remote source and detector, so as to provide a very slim flexible sensor which is useful where space is restricted, e.g. as a medical catheter probe.

10 Claims, 11 Drawing Figures

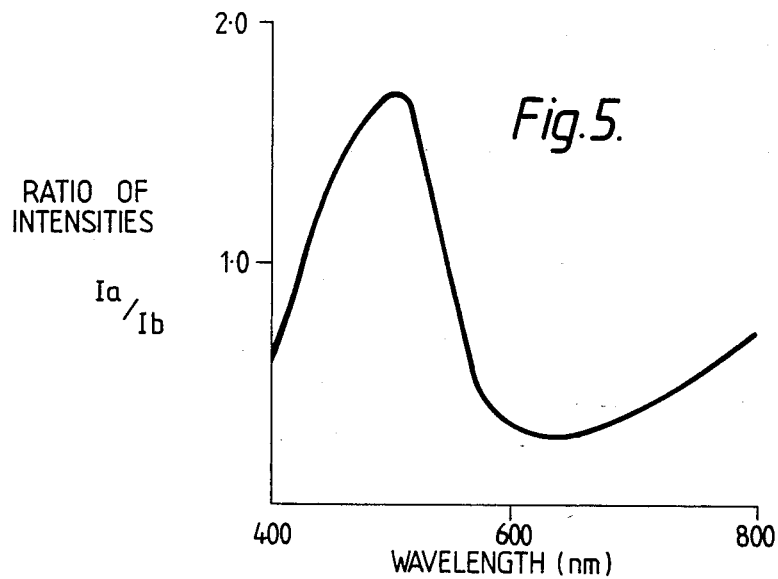
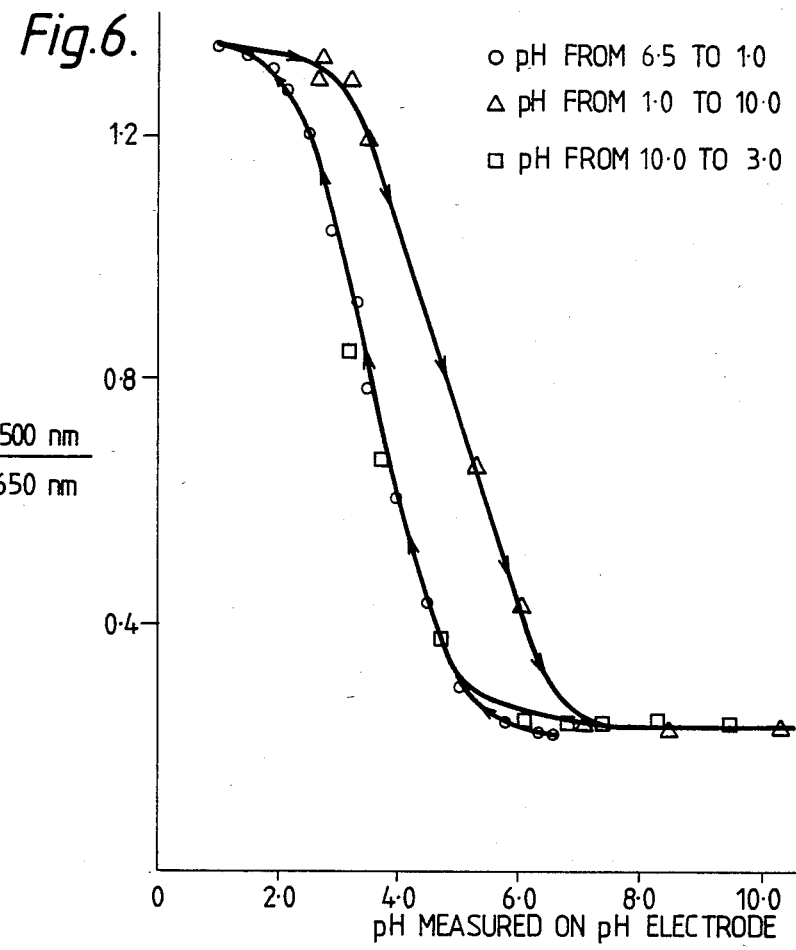

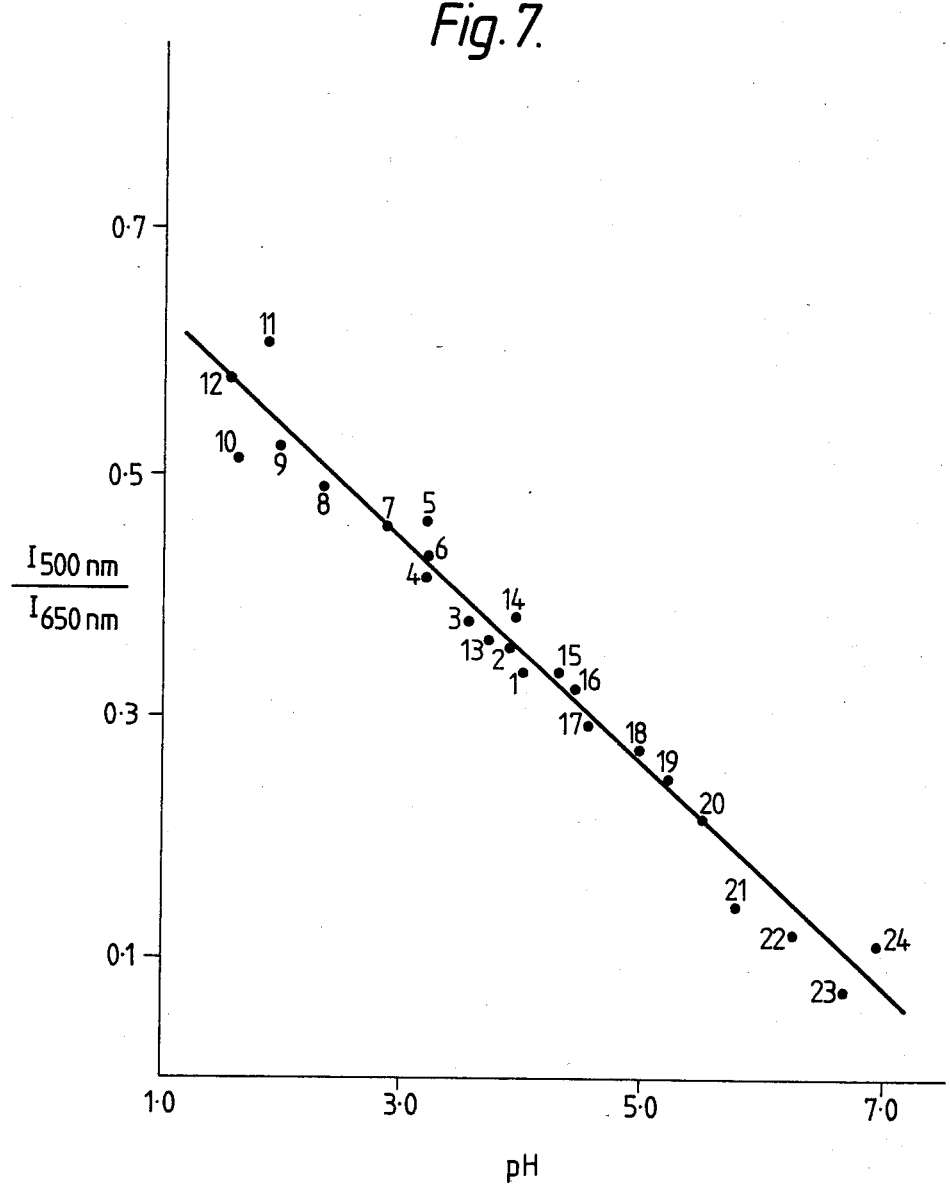

OPTICAL FIBRE SENSOR

The invention relates to sensors for detecting changes in chemical or physical parameters, using optical waveguide techniques.

It has been known for a long time that it is possible to alter the transmission properties of an optical waveguide by causing certain chemical reactions to occur in a closely surrounding coating layer. This is described, for example, in a paper by Hardy and David in Nature, Vol 257, Oct. 23, 1975, pages 666–667, and this technique has subsequently been refined as shown by later papers, e.g. vapour phase determination of blood ammonia by Smock et al, Analytical Chemistry, Vol 51, No 4, April 1979, pages 505–508. The technique which is common to all these papers is to use as waveguides, short (e.g. 10-20 mm) glass rods, 1 mm in diameter (although rods within the range 0.9–1.3 mm could be accommodated). The rods are coated with sensitive coatings which change colour quantitatively when exposed to specific chemicals (e.g. sodium picrate for cyanide or ninhydrin for ammonia), the sensitive material being held in a polymer matrix. The coating refractive index is greater than or equal to that of the rod so that light launched into the rod is propagated through the coating, the authors explaining how a lower refractive index is undesirable as it leads to propagation through the core, and hence lower sensitivity through the evanescent wave interactions occurring only in the region of the rod-coating interface. In order to launch light into such waveguides, a sophisticated optical system is used for providing the light in the form of a hollow cone, and the light is detected immediately as it emerges from the distal end of the coating by using a wide angle collector/detector system. This optical system would make the use of such waveguides for remote real-time monitoring of conditions on chemical or other industrial plants difficult and/or expensive, and makes them generally unsuitable for uses in confined spaces, such as in catheter probes for example. Unfortunately, there is no way of avoiding the use of such an optical system (so far as we are aware) when using such waveguides in the manner taught. The present invention utilises the principle of sensitive coatings to modify light transmitted through an optical core, but departs from the format which has been used for so long, by using a remote light source and detector, and by using a sensor in which the light transmission medium is substantially the same as that used to transmit light from the remote light source to the sensor and thence to the remote detector. In doing so we provide a new apparatus which overcomes, or at least substantially ameliorates, the above difficulties and restrictions, and which we find in practice also provides a number of further advantages.

According to the present invention, there is provided an apparatus for detecting changes in chemical or physical parameters, which comprises a sensing optical fibre comprising a core surrounded by a sensitive cladding whose absorption spectrum varies with changes in the chemical or physical parameters when these are applied to the cladding, and transmissive optical fibre means comprising a core surrounded by an insensitive cladding for connecting at least one end of the sensitive optical fibre to a remote light source and a remote detector, the core of the sensing optical fibre having substantially the same diameter as the core of the transmissive fibre means and the refractive indices of both the sensitive and the non-sensitive claddings having refractive indices that are lower than the refractive indices of the cores of both the sensing fibre and the transmissive optical fibre means.

The transmissive optical fibre means can be two optical fibres, one extending from one end of the sensitive fibre to be connected to the light source at its remote end, and the other extending from the other end of the sensitive fibre to be connected to the detector. Alternatively the transmissive optical fibre means can be a single optical fibre extending from one end of the sensitive fibre whose other end is made reflective. In this alternative form, the single optical fibre must then be connected to both source and detector, using beam splitters of appropriate kinds somewhere along its length, and various preferred apparatus configurations are described in more detail hereinbelow.

Optical fibres consist essentially of a thin flexible transparent core surrounded by a thin solid cladding of lower refractive index, in intimate contact with the core. Typical core diameters currently used are 200 $\mu$m, 100 $\mu$m and 60 $\mu$m, and as the core diameters of the transmissive and sensitive fibres are to be matched in the present apparatus, it will be appreciated that the present sensitive fibres are very much thinner than those of the previously known rod waveguides referred to above; and indeed the latter would not provide an effective sensor if modified by being fusion spliced to the much thinner optical fibres, particularly where all the light is propagated through the waveguide's sensitive cladding.

In the present apparatus, the light is propagated along the sensing fibre through its core, interrogating the sensitive cladding by its evanescent waves at each internal reflection. This manner of propagation is necessary for our device to operate, and in this it is in direct contrast with the cladding propagation of the known waveguides described above. However, we have also found in practice that we obtain other substantial advantages by using this previously despised form of propagation. Thus, for example, propagation through the cladding requires total internal reflection at the outer surface of the cladding. This being the outer surface of the fibre, it can easily become damaged, producing scatter centres and consequent loss of signal. Protection of that surface tends to be difficult as the variable parameters (e.g. pH of environmental liquid) requires free access to the sensitive coating to bring about the detectable changes. Our internally reflecting surface is never exposed to such damage, being protected by the sensitive cladding: a substantial advantage under arduous industrial plant conditions. Moreover we have not experienced problems due to low sensitivity as predicted by the above references. Indeed, because we propagate through optical fibre cores with their very high transparencies, we are able to use much longer sensitive fibres if necessary, and configurations taking advantage of this and also of the much greater flexibility of our thinner fibres, are described in more detail hereinafter. In general, however, this is not true when propagating through the cladding, with losses increasing exponentially through the much less transparent cladding material, and the previous rigid waveguides were generally restricted to short lengths, rods up to only 20 mm being disclosed.

Our preferred apparatus configuration is a probe having a reflective sensitive end, and a remote end connectable to both source and detector so that light fed into the remote end is transmitted to the sensitive end, and at least a portion is reflected back to the remote end for collection by the detector. This can be achieved in two particularly effective ways. In the first of these the core of the sensitive fibre is made reflective at one end and the transmissive optical fibre extends from the other end for conveying light both to and from the sensitive fibre, e.g. as a single optical fibre. This enables a particularly thin probe to be constructed, i.e. one having the thickness of the single optical fibre.

The sensitivity of this configuration is enhanced in that the light interrogates the sensitive cladding twice, i.e. both before and after reflection. However, as both the light source and detector need to interface the single transmissive fibre leaving the sensitive fibre, some form of beam splitter (e.g. a Y junction or half silvered mirror) will be required, and a substantial proportion of the signal may be lost there, dependent on the form of beam splitter employed. The beam splitter is conveniently positioned adjacent the source and detector, i.e. remote from the sensitive fibre, but less noise can sometimes be introduced by locating it adjacent the sensitive fibre i.e. remote from the light source. The reflective end can be a scattering surface, but as this generally results in loss of signal we prefer to flatten and polish the end to give substantially specular reflection in order to retain as much of the light as possible.

The second form of probe is an apparatus wherein the sensitive fibre has two ends each of which leads into a different transmissive fibre, the sensitive fibre being in the form of two portions lying adjacent each other and joined by a reflective coupling means whereby light launched from a source into the remote end of one transmissive fibre, travels through that fibre, through one portion of the sensitive fibre to be reflected into the other portion and thence along the other transmissive fibre for detection at the latter's remote end. This design does not require a beam splitter to separate ingoing and outgoing beams, and can still be formed as a very thin probe having a size substantially that of two optical fibres in one thickness direction and only a single fibre in the perpendicular directions.

Because of their small dimensions the probes can be inserted into liquid streams in quite narrow pipework without substantially affecting the fluid flow, for example to monitor continuously the pH of a liquid stream in a chemical plant, or they can be inserted through catheters into living organisms for remote real time monitoring. However a probe configuration is not the only configuration in which the present apparatus can be used. A configuration which can be particularly useful where a long sensitive fibre is required, is one comprising an optical fibre the ends of which are connectable to a light source and detector respectively, an intermediate portion having a sensitive cladding, i.e. a configuration similar to the second probe configuration described above except that the two portions form a single continuous fibre without any reflective break.

For increased sensitivity, we prefer an apparatus wherein the intermediate portion is in the form of a coil. We find that the increase in sensitivity is greater than that which would be expected by reason only of the increased length of fibres in a coil compared with a straight length of fibre equal to the length of the coil. This enhanced effect is noticed whether the coil is cylindrical, planar or in some intermediate configuration. In each case the coil should preferably be mounted so that adjacent turns are not touching, thereby to enable the fluid to come into intimate contact with the fibre throughout the whole length of the intermediate portion; although for a large coil it may be desirable to support the fibre at intervals to give the coil strength and rigidity.

A form of apparatus which enables complete immersion of the intermediate portion to be ensured, is one wherein the intermediate portion is located within a container for the fluid, and the end portions are connectable to a light source and detector outside the container. For monitoring a constant stream of fluid, a preferred apparatus is one wherein the container has separate inlet and outlet ports for the fluid, such that the fluid may flow through the container and completely immerse the intermediate portion of the fibre as it does so. For sampling a mass of fluid, a preferred apparatus is one having at least one port, and suction means for drawing a sample of the fluid into the container through the port.

One preferred form of cladding for the sensing fibre comprises a chemochromic material embedded in a solid carrier. A chemochromic material is one which changes colour or depth of colour in the presence of changing amounts of specific chemical elements, ions or compounds. As optical fibres can be made which are suitable for transmitting light in the ultraviolet, visible and infra-red regions, it is often useful to be able to use wavelengths outside the visible range. Hence in the present context we include within the term "chemochromic materials" those whose absorption spectra change within the ultraviolet, visible or infra-red ranges.

The change may be one which occurs abruptly when a certain concentration of the specific chemical is reached. Examples of chemochromic materials which change in this manner include some indicator dyes which are sensitive to hydronium ions and change colour at specific values of pH, or over narrow ranges of pH.

Mixtures of such dyes may be used to provide a universal indicator changing through a range of colours to give a direct indication of pH over a wide range of values.

Other chemochromic materials change colour gradually, where the depth of colour indicates the amount present of some specific chemical. Examples include materials used for colorimetric analysis. Thus metal ions can be detected by chelating compounds or other complexing agents capable of forming coloured complexes in the presence of the metal ions.

Various physical changes can also be detected or monitored by using the appropriate colour-changing material as the fibre cladding. Thus for example, temperature changes can be monitored using thermochromic materials such as liquid crystals.

The changes can be monitored so as to give an instantaneous measure of the parameter, by using a material for the cladding whose absorption spectrum changes in a reversible manner. Examples of these are the indicator dyes and the liquid crystals referred to above. In some cases a hysteresis effect may be observable with some dye/supporting polymer combinations, but this effect need not preclude such combinations from many continuous monitoring applications.

The apparatus can, however, also be used to indicate the full history of its environment, by using as cladding, a material which undergoes an irreversible colour change. For example a complexing agent held fast within the cladding may bind metal ions in a manner which is non-reversible in the environment of the measurement, so that the colour change will continue so long as further metal ions are being added to the environment. This can be useful for sampling a liquid stream for accumulative poisons, for example. When using such non-reversible agents, it can be helpful to select complexing agents which can be regenerated by changing the environment. A further type of non-reversibility which is not regeneratable, is one wherein the cladding is formed from a leachable coloured material. When this is placed in a stream containing a leaching agent, it can provide a measure of the total quantity of leaching agent passing within the period of the measurement.

We prefer the core of the sensitive fibre to be integral with the core of the transmissive fibre means. In such an apparatus there will automatically be no difference in core diameter between transmissive and sensitive fibres, and the possibility of any misalignment occurring when butt joining the ends of different cores is clearly avoided. This is most readily achieved in probe configurations of either of the above tapes, e.g. by removing a length of insensitive coating from one end of a transmissive fibre, and coating that end with sensitive material. In contrast to the core thickness, we find that the cladding thickness applied is this way is not critical. However to provide an intermediate portion with an integral core can present more difficulty, and we generally prefer to make an intermediate portion with sensitive cladding separately from the transmissive portions with their conventional non-sensitive cladding, and to join them together using standard connectors or by fusion splicing.

Where two cores are joined together, we prefer that they have substantially the same refractive index, thereby to avoid losses due to interboundary reflections. Where an integral core is used or where joined cores of substantially the same refractive index are used, we prefer that the refractive index of the sensitive cladding be substantially the same as that of the non-sensitive cladding, thereby to maintain a constant numerical aperture ($\sqrt{n_1^2 - n_2^2}$ where $n_1$ and $n_2$ are the refractive indices of the core and cladding respectively) where the sensitive fibre meets the transmissive fibre. Differences in numerical aperture values can lead to losses at the interface, and accordingly where substantial differences between the refractive indices of adjacent claddings cannot be avoided, we prefer to match such imbalance with a corresponding imbalance in core refractive indices so as to reduce, or preferably remove altogether, any change in numerical aperture values at the interface.

The invention is illustrated by reference to specific embodiments thereof shown in the accompanying drawings, in which:

FIGS. 3-7 are graphs obtained from experimental results.

Figure 1:
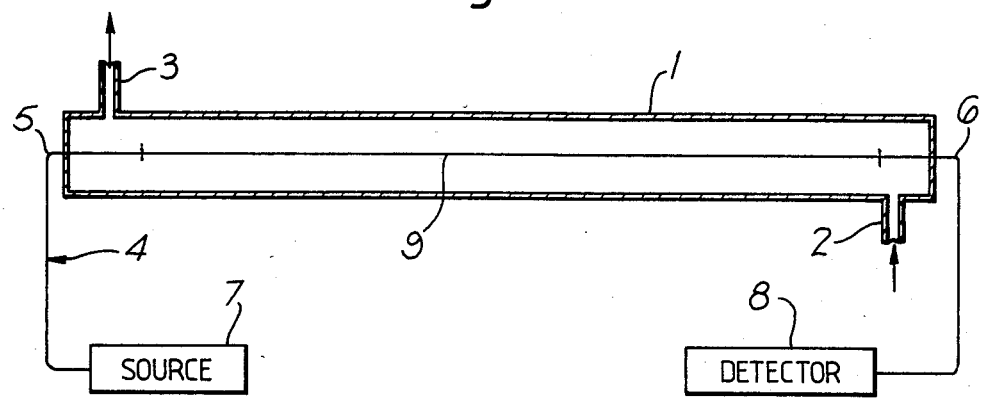
FIG. 1 is a section through an apparatus for detecting chemicals in a flowing liquid.

In FIG. 1 the apparatus comprises a tubular container 1 having an inlet port 2 and an outlet port 3. Sealed into the container is an optical fibre 4, the two ends portions 5, 6 of which have a layer of conventional cladding on their outer surfaces, and are connected to a light source 7 and detector 8, respectively. Welded to the two end portions, and located entirely within the tubular container, is an intermediate portion 9 whose cladding comprises a complexing agent which forms a coloured complex with transition metal ions, bound to the fibre core using a water swellable polymer.

In use, liquid flows through the container from the inlet port to the outlet port keeping the container sufficiently full for the intermediate portion of the fibre to remain continuously immersed in the liquid. The liquid contains metal ions which are to be monitored, and as these form a complex with the complexing agent in the cladding, the latter becomes coloured. Light is fed to the fibre from the source, and at each contact with the cladding/core interface, the evanescent wave penetrates the cladding to be partially absorbed according to the absorption spectrum of the complex in the cladding. In the apparatus of FIG. 1, the light source has a narrow bandwidth, emitting only at an absorption peak of the complex. The detector is a simple device which detects the total amount of light it receives. This will vary according to the amount absorbed as it passes through the intermediate portion, and hence provides a measure of the amount of complex formed.

Figure 2:
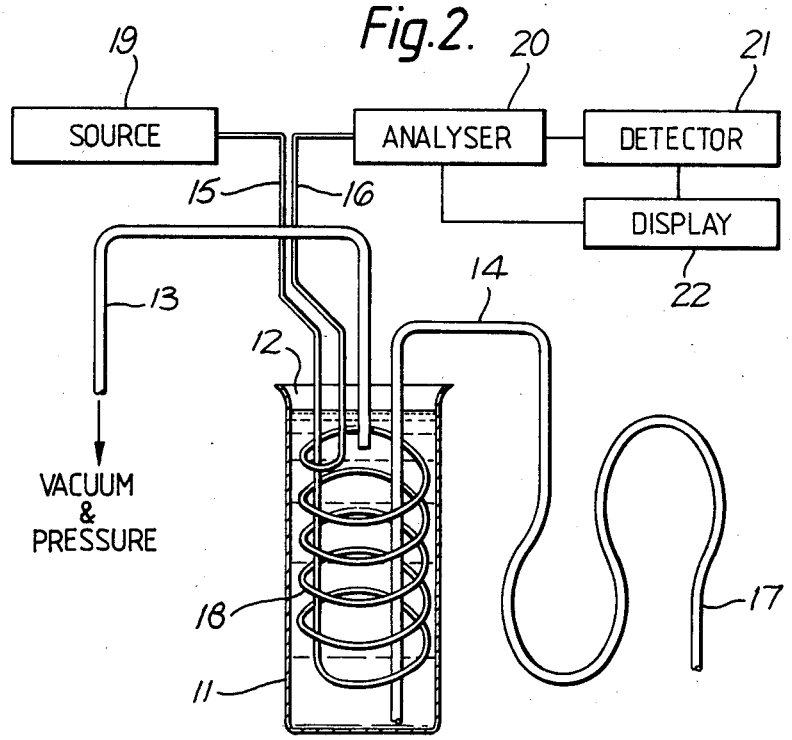
FIG. 2 is a section through an apparatus for sampling liquids.

The apparatus of FIG. 2 comprises a container 11 closed by a lid 12 through which pass a vacuum/pressure supply pipe 13, a sample pipe 14 and two end portions 15, 16 of a quartz optic fibre clad with conventional cladding material. The sample pipe is flexible and ends in a nozzle 17. Within the container is an intermediate portion 18 of the optical fibre, which is formed into a loose coil and joined to the end portions by standard connectors. Unlike that of the end portions the cladding of the intermediate portion comprises an indicator dye held to the core by a porous binder.

One end of the optical fibre is connected to a broad band light source 19, and the other end is connected to an analyser 20, which in turn is connected to a detector 21. The purpose of the analyser is to split up the broad band of light, scan the spectrum and send on to the detector only a narrow band at a time. In the embodiment of FIG. 2, a rotatable diffraction grating is used as the analyser, but other devices such as graduated filter discs could be used as alternatives. The analyser 20 and the detector 21 are both connected to a display 22, which correlates the detected intensity with the wavelength of the light detected.

In use the nozzle 17 is dipped into the liquid to be tested, and vacuum applied via the pipe 13, to suck the liquid into the container. This is continued until the coil of the intermediate portion is fully immersed in the liquid. Light is then passed through the fibre as before, but in this embodiment it is then analysed, detected and displayed, with the display showing the absorption at different wavelengths. At the conclusion of the measurement, the container may be emptied by applying pressure to the pipe 13.

As alternatives to the apparatus shown in the drawings, the flow-through container of FIG. 1 may be provided with a broad band source, analyser, detector and display as shown in FIG. 2, or the simplified optical system shown in FIG. 1 may also be used with the FIG. 2 container.

Figure 3:
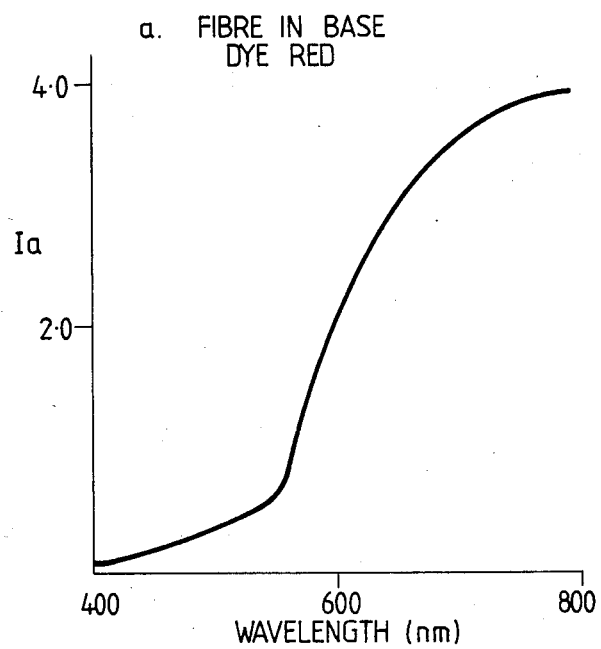
Figure 4:
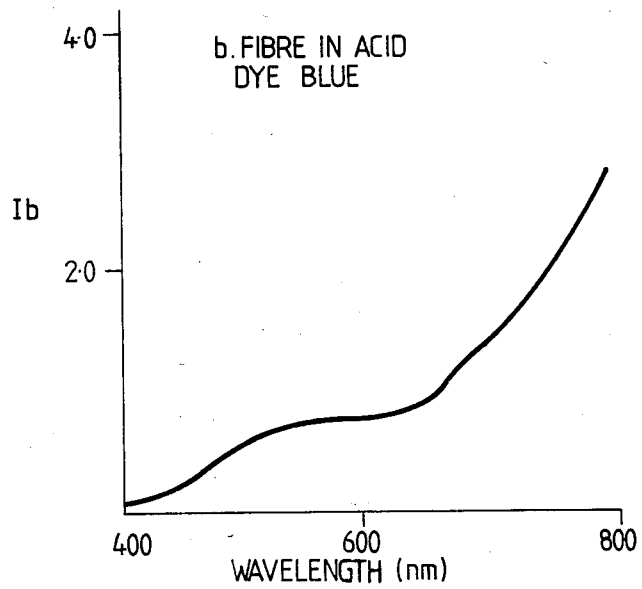

One of such alternatives was used to obtain the results shown in FIGS. 3 to 5. The container was a flow-through device similar to that shown in FIG. 1. The optical fibre had a quartz core with conventional cladding on the end portions 5,6 and a cladding of congo red indicator dye in cellulose acetate binder for the intermediate portion 9. The remainder of the optical system consisted of a light source 19 having a bandwidth covering the range 400 to 800 nm, a rotatable grating analyser 20, a detector 21 and a display 22 substantially as shown in FIG. 2.

The container was first filled with a base, totally immersing the intermediate portion of the fibre. Light covering the wavelengths 400 to 800 nm was passed through the fibre, analysed and the detected intensity plotted against wavelength. FIG. 3 shows the results obtained. The base was then replaced by an acid, and the results are shown in FIG. 4. In neither of these latter two figures was any correction made for the characteristics of the source or detector, so to eliminate these, the ratio of the two results was plotted against wavelength. The results are shown in FIG. 5.

Further experiments were carried out in an apparatus comprising a 100 ml beaker which had been modified by providing two pairs of ports near its base for receiving two optical fibres, and sealing them against loss of liquid from the beaker. The fibres extended across the beaker clear of its base and sides in a manner similar to the fibre held straight down the centre of the tube of FIG. 1. The provision of two pairs of ports was to allow two fibres to be examined simultaneously, but each pair of ports could be used on its own when only a single fibre was being investigated. The fibres had a sensitive intermediate portion about 5 cm long between their respective ports, and the two non-sensitive end portions of each fibre which emerged from the outside of the ports, were connected to a light source and detector respectively. The beaker was also provided with a stirrer and pH meter electrode.

The source used was a wide spectrum quartz-iodide lamp focussed onto a driven grating monochromator. The monochromator was driven through the spectrum, and the readings at 500 and 650 nm wavelengths were selected to give the ratio of intensities at an absorbed wavelength and at a substantially non-absorbed wavelength as reference. The light was modulated before being focussed onto the fibre using a rotating chopper, and a lock-in amplifier in the detector was locked to the same modulation frequency, thus avoiding errors from stray light sources. (Alternative sources which can be used are suitable two-colour light emitting diodes with electronic modulation. We have used red/green diodes quite successfully, but have quoted results using full spectrum means as the diode colours we had available were not optimised, resulting in lower sensitivity).

Two different sensitive fibres were examined. These were inserted in turn through one pair of ports, the beaker filled with buffer solution and titrated using 0.1N HCl or 0.1N NaOH solution, depending on the direction of pH movement desired. The pH was measured using the pH meter and this was plotted against the ratio of the intensities at the two wavelengths. One of the sensitive fibres was a 200 $\mu$m thick fibre clad in cellulose acetate doped with a methyl red derivative, the results being shown graphically in FIG. 6. The other was a similar fibre core clad in cellulose acetate doped with congo red indicator. The results of this latter experiment are shown graphically in FIG. 7. In both cases the cellulose acetate was water insoluble and so remained as cladding on the fibre throughout the experiment, but it was also water swellable. This enabled the solution to have free access to the dye molecules and it also resulted in a cladding of lower refractive index The polymer of the cladding was a commercially available cellulose acetate with a quoted acetic acid content of 55–56%.

As will be seen from FIG. 6 we obtained a hysteresis effect when using the methyl red derivatives as indicator, and for this reason the order in which the readings in FIGS. 6 and 7 were obtained is indicated in the drawings. Despite the hysteresis, this dye/polymer combination could be used effectively for controlling automatic neutralisation of acid streams, either alone or in combination with a further dye giving colour changes in the higher pH ranges to prevent over shooting.

As shown in FIG. 7, the intensity ratio of light at 500 nm. to that at 650 nm. with congo red in cellulose acetate cladding was found to be linear for all acid pH values, reproduceable colours being obtained without reference to the pH history of the solution, there being no hysteresis observed with this dye/polymer combination within this pH range, and consequently it is preferred for general purposes.

Figure 8:
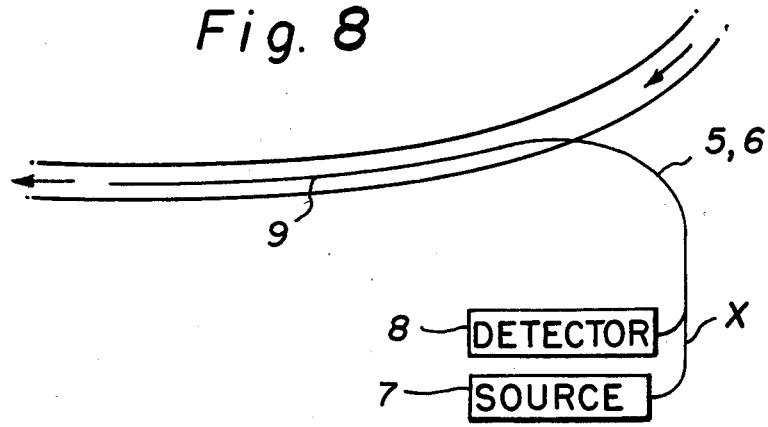
FIGS. 8-11 show further embodiments of the apparatus.
Figure 9:
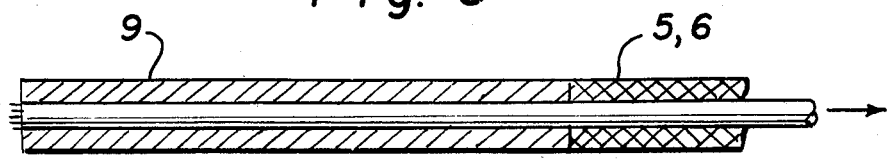
Figure 10:
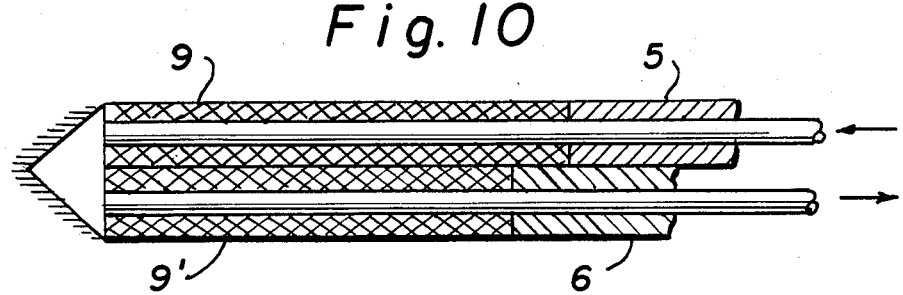

FIG. 8 shows a terminal probe, used in a FIG. 1 rather than a FIG. 2 type situation, i.e. where a slim probe is inserted into a conduit carrying a flowing liquid and requiring only a single penetration of the conduit wall. The transmissive optical fibers 5, 6 can either be a single fibre carrying both ingoing and outcoming signals and using a simple Y junction at X, or two separate fibers running side by side until they reach X, where they are allowed to separate and travel to their source and detector, respectively. The sensitive portions in these two cases are shown enlarged in FIGS. 9 and 10, respectively.

Figure 11:
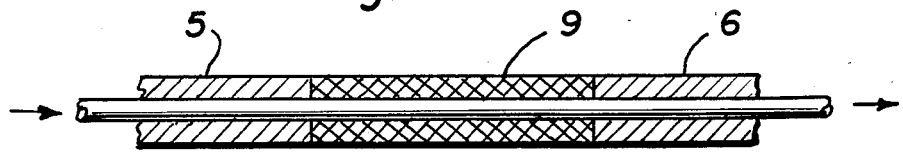

A fibre with an intermediate sensitive portion is shown in FIG. 11, being axially foreshortened and transversally expanded to demonstrate the core and its different end and intermediate claddings 5, 6 and 9.

We claim:

1. Apparatus for detecting changes in chemical or physical parameters, comprising:
   a sensing optical fibre including a core surrounded by a relatively sensitive cladding the absorption spectrum of which varies with changes in chemical or physical parameters when these are applied to said relatively sensitive cladding; and
   transmissive optical fibre means, including a core surrounded by a relatively insensitive cladding the absorption spectrum of which tends not to vary with changes in the chemical or physical parameters when these are applied to said relatively insensitive cladding, for connecting at least one end of the sensing optical fibre to a remote light source and a remote detector;
   the core of the sensing optical fibre having substantially the same diameter as the core of the transmissive fibre means; said relatively insensitive cladding refractive index being less than the refractive indices of the cores of both the sensing optical fibre and the transmissive optical fibre means.

2. Apparatus as claimed in claim 1, in the configuration of a probe having a reflective sensitive end and a remote end connectable to both said light source and said detector so that light fed into the remote end is transmitted to the sensitive end, and at least a portion thereof is reflected back to the remote end for collection by the detector.

3. Apparatus as claimed in claim 2 wherein:
   the core of the sensing optical fibre is made reflective at one end; and the other end of said sensing optical fibre extends from the transmissive optical fibre for conveying light both to and from the sensing optical fibre.

4. Apparatus as claimed in claim 2 wherein:

there are provided two sensing optical fibre portions each having an end which leads into a different transmissive fibre, these sensing optical fibre portions lying adjacent each other and joined by a reflective coupling means whereby light launched from source into the remote end of one transmissive fibre travels through that fibre, through one portion of the sensing optical fibre to be reflected into the other portion there and thence along the other transmissive fibre for detection at the remote end of said other transmissive fibre.

5. Apparatus as claimed in claim 1, wherein said sensing optical fibre is constructed and arranged to have opposite ends thereof connected to a light source and detector respectively via the transmissive optical fibre means, 6. Apparatus as claimed in claim 5 and further including:

a container of fluid;

wherein the sensing optical fibre is located within said container of fluid, and the end portions thereof are constructed and arranged to be connected via the transmissive optical fibre means to a light source and detector outside the container.

7. Apparatus as claimed in claim 5, wherein the sensing optical fibre is in the form of a coil.

8. Apparatus as claimed in claim 1, wherein:

the relatively sensitive cladding for the sensing optical fibre comprises a chemochromic material embedded in a solid carrier.

9. Apparatus as claimed in claim 8 wherein the chemochromic material comprises at least one pH sensitive dye and wherein the solid carrier comprises a water insoluble, water swellable material.

10. Apparatus as claimed claim 1, wherein:

the relatively sensitive cladding comprises a material which can quantitatively undergo an irreversible colour change when subjected to physical or chemical parameters.

* * * * *